United States Patent
Kaplan et al.

(10) Patent No.: US 8,500,647 B1
(45) Date of Patent: Aug. 6, 2013

(54) DATA-OPTIMIZED FILTER FOR IMAGE PROCESSING

(75) Inventors: Mitchell Kaplan, Lake Forest Park, WA (US); Clinton T. Siedenburg, Everett, WA (US)

(73) Assignee: SonoSite, Inc., Bothell, WA (US)

( * ) Notice: Subject to any disclaimer, the term of this patent is extended or adjusted under 35 U.S.C. 154(b) by 1152 days.

(21) Appl. No.: 11/411,655

(22) Filed: Apr. 26, 2006

(51) Int. Cl.
*A61B 8/00* (2006.01)

(52) U.S. Cl.
USPC ........... 600/455; 600/437; 600/407; 600/454; 600/453

(58) Field of Classification Search
USPC .................. 600/450, 453, 454, 455, 465, 468
See application file for complete search history.

(56) References Cited

U.S. PATENT DOCUMENTS

| | | | |
|---|---|---|---|
| 5,477,858 A * | 12/1995 | Norris et al. ................... | 600/441 |
| 2002/0169378 A1 * | 11/2002 | Mo et al. ....................... | 600/437 |
| 2003/0009102 A1 * | 1/2003 | Quistgaard et al. ........... | 600/446 |
| 2005/0054931 A1 * | 3/2005 | Clark ............................ | 600/453 |
| 2007/0236374 A1 * | 10/2007 | Brueske et al. ............... | 341/143 |
| 2008/0130964 A1 * | 6/2008 | Zwirn et al. .................. | 382/128 |

OTHER PUBLICATIONS

Kruse et al (A new high resolution color flow system using an eigendecomposition-based adaptive filter for clutter rejection).*
Dustin E. Kruse & Katherine W. Ferrara, "A New High Resolution Color Flow System Using an Eigendecomposition-Based Adaptive Filter for Clutter Rejection," IEEE Transactions on Ultrasonics, Ferroelectrics, and Frequency Control, vol. 49, No. 12, Dec. 2002, 1739-1754.

\* cited by examiner

*Primary Examiner* — Tse Chen
*Assistant Examiner* — Joel F Brutus

(57) ABSTRACT

A system and method are provided for producing a signal filter to block clutter. An embodiment includes the steps of acquiring samples of a clutter signal, calculating eigenvectors and eigenvalues representing the clutter signal, comparing said eigenvalues to a threshold to distinguish between eigenvectors representing clutter and those representing noise or signal, and determining filter parameters using the comparison results. Embodiments of the invention allow for optimization of wall filters for different anatomical applications, such as different body parts, in ultrasound imaging. The clutter signal may include Doppler data, and may be acquired using a pulsed wave (PW) mode, although the filter itself may be used in scanning Doppler color mode. The resulting wall filter is optimized for blocking clutter that is comparable to the clutter of the sampled clutter signal.

38 Claims, 1 Drawing Sheet

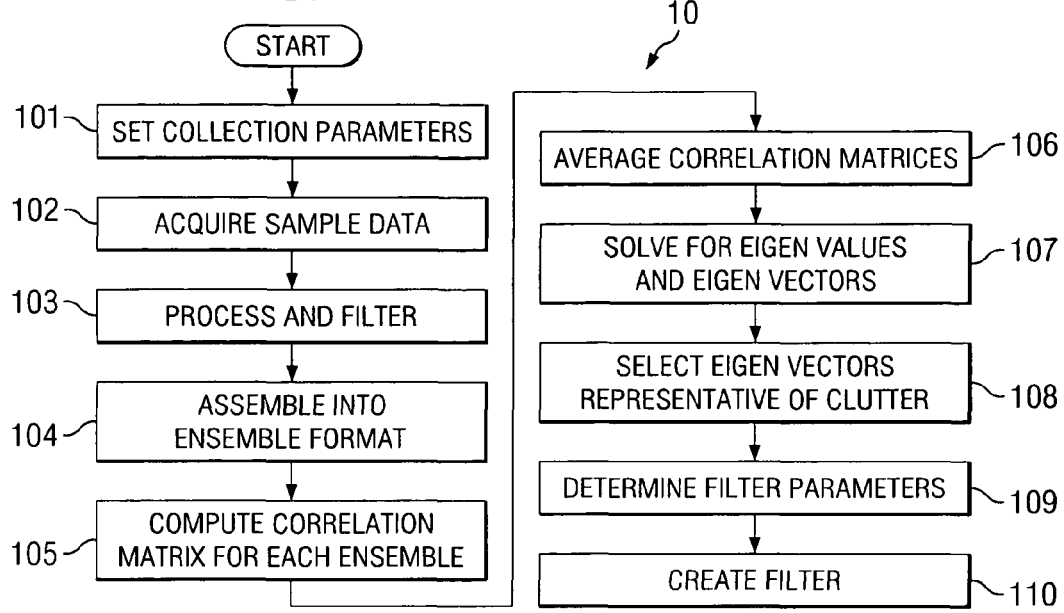
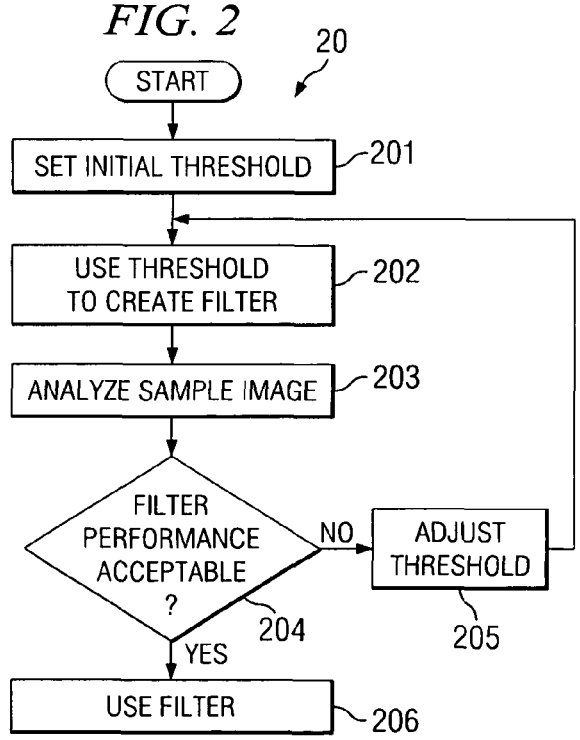
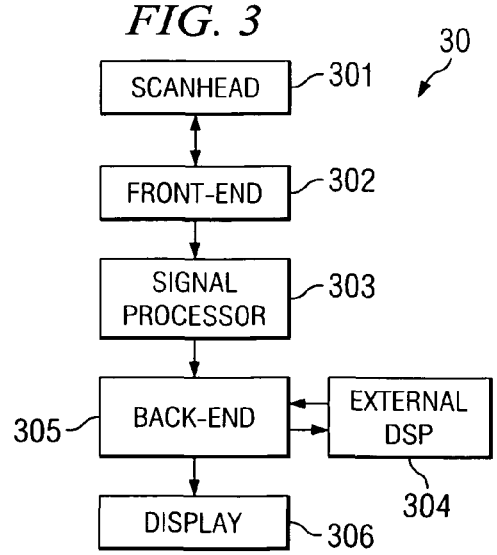

DATA-OPTIMIZED FILTER FOR IMAGE PROCESSING

TECHNICAL FIELD

The invention relates generally to signal processing, and more particularly, to determining filter parameters for processing of ultrasound images.

BACKGROUND OF THE INVENTION

Ultrasound equipment may be used for measuring the velocity and other characteristics of blood flow, by using Doppler color mode processing for diagnostic imaging. Unfortunately, the signals of interest often have lower amplitudes than signals from other objects within the same imaging field. Such signals, which include reflections from large, stationary objects or even large, slow-moving objects, are often not of interest in Doppler color mode processing. These unwanted signals are called clutter signals, and color mode processing detection must often discriminate against such clutter signals.

Filters are generally used to reject clutter signals, which then allows detection of relatively weak signals of interest. Clutter rejection filters, however, should pass the signals of interest without undue attenuation. Since a relatively small number of samples may be used in Doppler color mode processing, the transient response of the filters must be carefully controlled. For example, a typical system may attempt to estimate blood velocity with only 8 to 16 ultrasound pings. This provides challenges in designing a filter that effectively discriminates between large stationary signals and the small signals of interest. If the filter is ill-suited to the specific application, it may either fail to block enough clutter, or else block the signals of interest.

Previous solutions include using a single filter for all anatomical regions. Although the filters have been theoretically optimized for desirable mathematical properties, they may not be truly optimum for all applications. Typical solutions use a two-dimensional (2D) matrix filter, and attempt to minimize the transient response. One possible approach is described by Dustin E. Kruse & Katherine W. Ferrara, *A New High Resolution Color Flow System Using an Eigendecomposition-Based Adaptive Filter for Clutter Rejection*, IEEE Transactions on Ultrasonics, Ferroelectrics, and Frequency Control, Vol. 49, No. 12, Dec. 2, 1739-1754, the entire disclosure of which is hereby incorporated by reference.

BRIEF SUMMARY OF THE INVENTION

Embodiments of the invention provided for an ultrasound system using a signal filter that is optimized based on measured clutter signals. A characterization of sampled clutter signals is preferably used to determine filter parameters. The resulting filter is then optimized for blocking clutter that is similar to the clutter of the sampled clutter signal. The characterization process of a preferred embodiment includes sampling, filtering, noise rejection, and thresholding. Samples may be acquired using a different mode than the one for which the filter is being produced. One reason to use a different mode would be to acquire samples after transient responses have faded. Embodiments may use multiple subjects for the clutter samples and/or be dynamically tailored to a specific subject.

Embodiments of the invention provided for an ultrasound system using one or more signal filters, with each filter optimized for a specific anatomical application. Producing the filters may include acquiring samples of a clutter signal within the target anatomical application, calculating eigenvectors and eigenvalues representing the clutter signal, comparing the eigenvalues to a threshold to distinguish between eigenvectors representing clutter and those representing noise or signal, and determining filter parameters using the comparison results. The clutter samples may be acquired using a pulsed wave (PW) mode, although the filter itself may be used in scanning Doppler color mode. Filter creation may also be optimized using an iterative test and analyze process.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIG. 1 shows a flow diagram of operation according to an embodiment of the invention for creating a filter;

FIG. 2 shows a flow diagram of operation according to an embodiment of the invention for optimizing the threshold; and FIG. 3 shows a block diagram of an embodiment of the invention.

DETAILED DESCRIPTION OF THE INVENTION

FIG. 1 shows flow diagram 10, showing operation for creating a filter, according to an embodiment of the invention. Process 10 operates to create a wall filter tailored to a specific anatomical application. Process 10 generally shows sub-processes of collecting and conditioning data samples which include signals similar to those that are to be blocked by a filter, characterizing the samples using a set of basis functions, selecting the basis functions which represent signals to be blocked, and specifying filter parameters based on these selected basis functions.

Specifically, collection parameters, such as collection mode and pulse-repetition frequency (PRF), are set at box 101 to begin acquiring sample data at box 102 using an ultrasound system. Samples are processed and filtered to reduce noise at box 103, and assembled into ensemble format at box 104. Processing of the signals may include quadrature bandpass (QBP) filtering of the real and imaginary (in-phase and quadrature phase, I&Q) signal components, and may also include low-pass filtering to suppress random noise.

Ensemble is a term that describes a collection of data used in ultrasound Doppler processing. A representative ensemble, $\vec{X}_k$, is shown in equation (1). For typical ultrasound Doppler color mode applications, an ensemble may contain 8 to 16 complex data samples acquired from a series of echoes from the same spatial location. Some ultrasound systems may use more or fewer samples. Ultrasound pings may be sent out at a specific PRF, allowing for multiple echoes from the same location. Each sample is composed of an I&Q component, and represents a portion of a filtered ultrasound echo signal. Typically, each ensemble member is composed of an entire line of echo data, representing sampled echoes along a particular line emanating from the transducer. The ensemble is a collection of such lines of data acquired at the PRF. Data acquired in Doppler color mode may already be in ensemble format, but if sample data is collected in pulse wave mode (PW), the data may be reformatted as provided at box 104.

For an ensemble of length L, a finite impulse response (FIR) wall filter will be represented by an L×L matrix of filter coefficients.

$$\vec{X}_k = [x_k^0, x_k^1, x_k^2, \ldots, x_k^L] k=1,2,\ldots,K \tag{1}$$

According to a preferred embodiment, a number, K, ensembles are created, each of length L. K may be chosen based on the number of data ensembles desired for subsequent averaging.

For each ensemble, the L×L correlation matrix $R_k$ is preferably computed at box 105, using any acceptable means. As an example, the outer product may be used for the computation, as shown in equation (2).

$$R_k = \vec{X}_k \vec{X}_k^* \tag{2}$$

As an optional step, the K correlation matrices may be averaged at box 106, which may improve the estimate of the clutter.

The averaged correlation matrix, or alternatively, a single correlation matrix, is then preferably diagonalized by solving for eigenvalues and eigenvectors at box 107. The eigenvalue-eigenvector representation is shown in equation (3), and provides a representation of the data according to a set of basis functions.

$$\langle R_k \rangle = \frac{1}{K} \sum_k R_k = V \Lambda V^* \tag{3}$$

The spectrum of eigenvalues, the diagonal elements of Λ, is preferably thresholded at box 108 to produce a weight matrix, W. The significant eigenvectors exceeding a threshold are assumed to represent strong clutter returns which the resulting filter should block, while the eigenvectors below the threshold represent signals that the filter should pass. However, values near the filter may be afforded a degree of uncertainty. In W, therefore, 1's represent eigenvalues exceeding the threshold by a certain margin, 0s represent eigenvalues falling below the threshold by a certain margin, and scalar values between 0 and 1 represent eigenvalues that are close to the threshold value. This selects the significant eigenvectors to be used in determining filter parameters at box 109. A tailored filter may then be created at box 110 using the sampled data. One way to determine filter parameters would be to project the clutter signal onto a sub-space spanned by the dominant eigenvectors (those whose eigenvalues exceed the threshold), by computing a projection matrix, $P_T$, according to equation (4). Then, $P_T$ may be subtracted from the identity matrix to create F, an L×L matrix of filter coefficients, as shown in equation (5).

$$P_T = VW(VW)^* = V_T V_T^* \tag{4}$$

$$F = 1 - P_T \tag{5}$$

The filter that is produced may be a wall-filter, as is commonly used in ultrasound processing. Data may be collected in either PW or Doppler color mode processing, and the filter may be used in a different operational mode than was used for clutter sample collection. One reason to use a different mode would be to acquire samples after transient responses have faded. A filter thus created can be adaptive in the sense that it is based on measured data and designed optimally to suppress unwanted signals similar to those in a sample set. This is in contrast to the previous one-size-fits-all filter design or selection method.

Pre-filtering or preconditioning the samples after QBP processing can suppress random noise, while retaining salient spectral information. Suppressing noise and spurious signals prior to eigenvector decomposition will generally improve the clutter signal estimates, resulting in a higher quality filter. If the data is collected in PW mode, it may be reformatted into ensemble mode, which is a format often used for Doppler color mode data collection. There may be enough PW data to form multiple ensembles. However, the length of the ensembles may need to be the same as those collected during Doppler color mode when the filter is being used.

PW mode may be a preferred mode for sample collection, since the longer collection time allows transient responses to fade away so that data can be collected in a steady state. This then allows a truer representation of the clutter that is to be used for creating the filter coefficients. A common way to compute a correlation matrix is to use the outer product of the ensemble. If multiple ensembles were available, due to the number of samples collected, the average of their correlation matrices may provide a more reliable, lower-noise representation of the clutter signals. Diagonalizing a correlation matrix, or the average correlation matrix, allows representation of the signals in using eigenvectors and eigenvalues.

The eigenvectors represent various signals as a set of basis functions, while the corresponding eigenvalues represents the relative strength of the signals. Other basis function representations may also be used. Since sample data may be collected near large clutter sources, and clutter signals are assumed to be larger than the signals of interest, larger eigenvalues are assumed to correspond to clutter signals, according to an embodiment of the invention. A threshold applied to the eigenvalues may then be used to classify corresponding eigenvectors as either clutter signals to be filtered out, or target signals to be passed by the filter. A higher threshold will cut off more signals than a lower threshold. If the target signals, or signals of interest, indicate objects with a higher velocity than do the clutter signals, the resulting filter is a high-pass filter.

According to an embodiment of the invention, clutter samples may be collected from multiple subjects and used to produce a selection of pre-defined filters, each optimized for different anatomical applications. The samples are collected from known sources of clutter, such as a heart wall, and may generally be collected using a PRF similar to the one that will be used when the filter is operating on the Doppler color mode data. Various filter use scenarios can be used for different optimizations, such as different body parts, different subject classifications including age and gender, different PRFs, and varying combinations thereof.

Filters produced in this manner may still be updatable or adjustable, when new data is available to replace or adjust filter parameters. Such updating or adjusting may even occur dynamically in real-time or near real-time, where the actual structure that is present during use of the filter is used to produce the filter. For example, embodiments of the invention could generate or optimize a filter dynamically for a particular subject. In this mode of use, ultrasound equipment would be used in to perform process 10 for a particular test subject, and a tailored filter would be produced for the same or possibly different ultrasound equipment. Diagnostic ultrasound imaging could then be performed on the test subject using the tailored filter. Further, embodiments of the invention may allow for refining the filter during use. Some of the possible approaches for refining the filter include using additional clutter samples and adjusting a threshold, as described below.

Since selection of the threshold influences filter performance, embodiments of invention may include an iterative process for determining a threshold, such as using various trial levels until optimum filter performance is achieved. With appropriate feedback or iterative steps and an image analysis step, the selection of a particular threshold could be optimized, either with or without human operator involvement. FIG. 2 shows flow diagram 20 for optimizing a threshold according to an embodiment of the invention. An initial threshold is set at box 201 and used to create a first test filter at box 202. The results of this first filter are analyzed at box 203 using a sample image. If the filter performance is not acceptable, a decision at box 204 will result in adjusting the threshold at box 205 to a new trial value. Otherwise, the filter can be used at box 206.

FIG. 3 shows block diagram 30 of an embodiment of the invention. Scan head 301 couples to signal processor 303 through front-end 302. Signal processor 303 then outputs a signal to back-end 305, which interfaces with external digital signal processor (DSP) 304, and provides for viewing the image on display 306.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An ultrasound system comprising:
a scan head configured to acquire sample datasets from a subject; and
a signal processor communicatively coupled to the scan head, the signal processor configured to:
receive a first number of sample datasets from the scan head that represent lines of echo data through an anatomical region of interest;
computing a correlation matrix for each dataset;
computing an averaged correlation matrix from the correlation matrices associated with each of the datasets;
diagonalizing the averaged correlation matrix into a set of eigenvalues and eigenvectors;
producing a weighted matrix that corresponds to the set of eigenvalues having weights with a value of 1 if a corresponding eigenvalue exceeds a threshold value plus a first margin, the value of 1 indicating that the corresponding eigenvector represents a component of a clutter signal;
a weight value with a value of 0 if a corresponding eigenvalue falls below the threshold value minus a second margin, the value of 0 indicating that the corresponding eigenvector does not represent a component of the clutter signal; and
a weight value with a value between 0 and 1 if a corresponding eigenvalue falls between the threshold value minus the second margin and the threshold value plus the first margin, the value between 0 and 1 representing a measure for the degree to which the corresponding eigenvector represents a component of the clutter signal;
computing a projection matrix from the eigenvectors and the weighted matrix; and
subtracting the projection matrix from an identity matrix to determine a set of coefficients for a first signal filter to remove clutter from echo signals received from the anatomical region of interest.

2. The ultrasound system of claim 1, wherein the first signal filter comprises a wall filter.

3. The ultrasound system of claim 1, wherein the first signal filter is generated automatically.

4. The ultrasound system of claim 1, wherein the signal processor is further configured to refine the first signal filter during use.

5. The ultrasound system of claim 4, wherein refining the first signal filter during use comprises receiving an additional sample dataset from the scan head.

6. The ultrasound system of claim 1, wherein the clutter signal is associated with an object that has a lower velocity than an object of interest in the first anatomical region of interest.

7. The ultrasound system of claim 1, wherein the clutter signal is associated with one or more of a heart valve, a myocardium, an arterial wall, and a stationary structure within the first anatomical region of interest.

8. The ultrasound system of claim 1, wherein the first number of sample datasets comprise Doppler data, the Doppler data representing a velocity of an object of interest relative to the scan head.

9. The ultrasound system of claim 1, wherein the first number of sample datasets comprise pulsed wave (PW) mode data.

10. The ultrasound system of claim 9, wherein the first signal filter is operable to filter sample datasets acquired using a scanning Doppler color mode.

11. The ultrasound system of claim 1, wherein the signal processor is further configured to:
receive a second sample dataset from the scan head, the second sample dataset associated with a second anatomical region of interest;
calculate one or more filter parameters associated with the second anatomical region of interest;
generate, based on the calculated filter parameters, a second signal filter, the second signal filter configured to remove the isolated clutter signal from sample datasets associated with the second anatomical region of interest.

12. The ultrasound system of claim 11, wherein the first signal filter and the second signal filter are configured to be applied to sample datasets acquired using a mode different from the mode for which the first signal filter and the second signal filter are generated.

13. The ultrasound system of claim 11, wherein the scan head acquires the first sample datasets from a first subject and acquires the second sample datasets from a second subject.

14. The ultrasound system of claim 1, wherein the signal processor is further configured to:
receive a third sample dataset, the third sample dataset associated with the first anatomical region of interest; and
apply the first signal filter to the third sample dataset to generate a filtered dataset, the application of the first signal filter removing the isolated clutter signal from the third sample dataset.

15. The ultrasound system of claim 14, further comprising: a display communicatively coupled to the signal processor, the display configured to display the filtered dataset to a user as an ultrasound image.

16. A method of operating an ultrasound system to produce a signal filter, the method comprising:
receiving first sample datasets from an ultrasound scan head, the first sample datasets associated with a first anatomical region of interest;
calculating with a processor one or more filter parameters associated with the first anatomical region of interest by:
computing a correlation matrix for each dataset;
diagonalizing a correlation matrix into a set of eigenvalues and eigenvectors;
producing a weighted matrix that corresponds to the eigenvalues wherein:
a weight value has a value of 1 if a corresponding eigenvalue exceeds the threshold value plus a first margin, the value of 1 indicating that the corresponding eigenvector represents a component of a clutter signal,
a weight value has a value of 0 if a corresponding eigenvalue falls below the threshold value minus a second margin, the value of 0 indicating that the corresponding eigenvector does not represent a component of the clutter signal; and
a weight value has a value between 0 and 1 if the corresponding eigenvalue falls between the threshold value minus the second margin and the threshold value plus the first margin, the value between 0 and 1 representing a measure for the degree to which the corresponding eigenvector represents a component of the clutter signal;
computing a projection matrix from the eigenvectors and the weighted matrix; and
subtracting the projection matrix from an identity matrix to calculate a set of coefficients for a first signal filter to remove clutter from echo signals received from the anatomical region of interest; and
generating a first signal filter based on the calculated filter coefficients, the first signal filter configured to remove the clutter signal from sample datasets collected from the first anatomical region of interest.

17. The method of claim 16, further comprising assembling the first sample datasets into an ensemble.

18. The method of claim 16, further comprising receiving one or more additional sample datasets and assembling the additional sample datasets into one or more additional ensembles.

19. The method of claim 18, further comprising computing a correlation matrix for each of the additional ensembles.

20. The method of claim 16, wherein computing the correlation matrix comprises calculating an outer product.

21. The method of claim 16, further comprising finding an average correlation matrix based on the correlation matrices.

22. The method of claim 21, wherein calculating eigenvectors and eigenvalues of the correlation matrix is performed on the average correlation matrix.

23. The method of claim 16, wherein the first sample datasets are filtered prior to calculating the filter coefficients.

24. The method of claim 23, wherein the filtering comprises quadrature bandpass (QBP) processing.

25. The method of claim 24, wherein the filtering further comprises low pass filtering after the QBP processing.

26. The method of claim 16, wherein receiving the first sample datasets from an ultrasound scan head comprises receiving Doppler data.

27. The method of claim 16, wherein receiving the first sample datasets from an ultrasound scan head comprises receiving pulsed wave (PW) mode data.

28. The method of claim 16, wherein the first signal filter comprises a wall filter.

29. The method of claim 16, wherein the first signal filter is produced for scanning Doppler color mode data by using data collected in pulsed wave (PW) mode.

30. The method of claim 16, wherein the clutter signal is associated with clutter objects with lower velocity than an object of interest in the anatomical region of interest.

31. The method of claim 16, wherein the clutter signal is associated with one or more of a heart valve, a myocardium, an arterial wall, and a stationary structure within the anatomical region of interest.

32. The method of claim 30, wherein the object of interest is blood.

33. The method of claim 16 further comprising:
receiving a second set of sample datasets from an ultrasound scan head, the second set of sample datasets associated with a second anatomical region of interest;
calculating, one or more filter parameters associated with the second anatomical region of interest; and
generating a second signal filter based on the second calculated filter parameters, the second signal filter configured to remove the clutter signal from sample datasets collected from the second anatomical region of interest.

34. The method of claim 33, wherein the first sample datasets are collected from a first subject and the second sample datasets are collected from a second subject.

35. The method of claim 16, wherein the first sample datasets are received in a first mode and the first signal filter is used in a second mode.

36. A method of operating an ultrasound system to generate an ultrasound image, the method comprising:
receiving a first set of sample datasets from an ultrasound scan head, the first set of sample datasets associated with an anatomical region of interest;
calculating with a processor one or more filter coefficients associated with the anatomical region of interest by:
computing a correlation matrix for each dataset;
computing an average correlation matrix from the correlation matrices
diagonalizing the average correlation matrix into a set of eigenvalues and eigenvectors;
producing a weighted matrix corresponding to the eigenvalues with:
a weight value of 1 if a corresponding eigenvalue exceeds the threshold value plus a first margin, the value of 1 indicating that the corresponding eigenvector represents a component of a clutter signal, a weight value of 0 if a corresponding eigenvalue falls below the threshold value minus a second margin, the value of 0 indicating that the corresponding eigenvector does not represent a component of the clutter signal; and a weight value between 0 and 1 if a corresponding eigenvalue falls between the threshold value minus the second margin and the threshold value plus the first margin, the value between 0 and 1 representing a measure for the degree to which the corresponding eigenvector represents a component of the clutter signal;

computing a projection matrix from the eigenvectors and the weighted matrix; and subtracting the projection matrix from an identity matrix to determine a set of coefficients for a filter to remove clutter from echo signals received from the anatomical region of interest;

receiving a second sample dataset from the ultrasound scan head, the second sample dataset associated with the anatomical region of interest;

applying the generated signal filter to the second sample dataset to create a filtered dataset; and displaying the filtered dataset to the user as an ultrasound image.

37. The method of claim 36, wherein the first sample datasets are acquired from the anatomical region of interest of a first subject.

38. The method of claim 36, wherein the second sample datasets are acquired from the anatomical region of interest of a second subject.

* * * * *